United States Patent [19]

Nishio et al.

[11] Patent Number: 4,872,460

[45] Date of Patent: Oct. 10, 1989

[54] NONCONTACT TYPE TONOMETER

[75] Inventors: Kouji Nishio; Yoshihiko Hanamura, both of Tokyo, Japan

[73] Assignee: Tokyo Kogaku Kikai Kabushiki Kaisha, Tokyo, Japan

[21] Appl. No.: 87,039

[22] Filed: Aug. 19, 1987

[30] Foreign Application Priority Data

Aug. 21, 1986 [JP] Japan ................................ 61-195832
Aug. 21, 1986 [JP] Japan ................................ 61-195833

[51] Int. Cl.4 ............................................ A61B 3/16
[52] U.S. Cl. .................................... 128/648; 307/141
[58] Field of Search .............. 128/648, 745, 793, 652; 307/141; 62/158

[56] References Cited

U.S. PATENT DOCUMENTS 3,538,754 11/1970 Grolman et al. .
3,756,073 9/1973 Lavallee et al. .
3,818,241 6/1974 Ishizaka et al. .................... 307/14 X
4,665,923 5/1987 Kobayashi .......................... 128/648
4,724,843 2/1988 Fisher ................................ 128/648

FOREIGN PATENT DOCUMENTS

58-34128 7/1983 Japan .

Primary Examiner—William E. Wayner
Attorney, Agent, or Firm—Finnegan, Henderson, Farabow, Garrett & Dunner

[57] ABSTRACT

A noncontact type tonometer includes a fluid discharging device for discharging a fluid towards the cornea of an eye to be tested; an alignment detecting device for detecting an alignment between the axis of a fluid discharge of the fluid discharging device and the vertex of the cornea and for outputting an alignment signal; and a controlling device for determining whether or not the alignment has been completed upon receipt of the alignment signal from the alignment detecting device and outputting an alignment completion signal when the alignment has been completed. A fluid discharge of the fluid discharging device is automatically performed based on the alignment completion signal. The controlling device is provided with a monitoring device for monitoring the establishment of the alignment completion state for a predetermined time based on the alignment completion signal and outputting an action command signal for automatically performing the fluid discharge towards the fluid discharging device only when the alignment completion state has been maintained for the predetermined time.

7 Claims, 4 Drawing Sheets

NONCONTACT TYPE TONOMETER

BACKGROUND OF THE INVENTION

1. Field of the Invention

This invention relates to an improvement of a noncontact type tonometer including a fluid discharging means for discharging a fluid towards the cornea of an eye to be tested, an alignment detecting means for detecting an alignment between the axis of a nozzle discharging a fluid discharged from the fluid discharging means and the vertex of the cornea and outputting an alignment signal, and a controlling means for determining whether or not the alignment has been completed upon receipt of the alignment signal from the alignment detecting means and outputting an alignment completion signal when the completion of the alignment has been determined, a fluid being automatically discharged from the fluid discharging means based on the alignment completion signal.

2. Prior Art of the Invention

A conventional noncontact type tonometer is disclosed, for example, in Japanese patent publication 58-34128. This conventional noncontact type tonometer includes an apparatus as a fluid discharging means for discharging a fluid towards the cornea of an eye to be tested, an alignment detecting means for detecting a completion of an alignment between the axis of the nozzle of the fluid discharging apparatus and the vertex of the cornea, and a controlling means for determining whether or not the alignment has been completed upon receipt of the alignment signal from the alignment detecting means and outputting an alignment completion signal when the completion of the alignment has been determined.

The alignment detecting means is designed as such that infrared rays are projected towards the cornea from the axial direction of the afore-mentioned apparatus, the infrared rays reflected by the cornea in the axial direction is received by a photoelectrically inverting element, and an alignment signal corresponding to the amount of the reflected infrared rays received by the photoelectrically inverting element is output.

The controlling means is adapted to compare a signal value corresponding to the amount of the reflected infrared rays received by the photoelectrically inverting element with a preset signal value corresponding to the amount of light received by the photoelectrically inverting element when the vertex of the cornea is in alignment with the axis, and output the alignment completion signal when the differential signal value is less than a predetermined value. Accordingly, the controlling means outputs an alignment completion signal when the alignment between the axis of the apparatus and the vertex of the cornea has been completed and automatically projects an air pulse as a fluid towards the cornea of the eye to be tested from the afore-mentioned apparatus. The pressure of the eye to be tested is measured based on the time from when the air pulse is projected towards the cornea from the axial direction until when the cornea is caused to be applanation.

However, in the conventional noncontact type tonometer, sometimes it happens that the fluid discharging means starts discharging a fluid in spite of the fact that an alignment between the vertex of the cornea and the axis of the apparatus has not been completely performed. Namely, sometimes it happens that the patient looks aside or the patient slightly fluctuates the fixation of his sight during the alignment verification. In such a case as just mentioned, according to the conventional noncontact type tonometer, sometimes it happens that a completion of the alignment is determined by chance, an alignment completion signal is output from the controlling means, although it happens only in a moment, and the fluid discharging means starts discharging an air pulse as a fluid towards the cornea of the eye to be tested based on the alignment completion signal. As a result, such obtained eye pressure measuring value contains a measuring error or errors due to the patient's side looking, the patient's minor fluctuation of the fixation of his sight, or the like.

Furthermore, the conventional noncontact type tonometer has the additional disadvantage in that after an air pulse as a fluid had been discharged based on the alignment completion signal and the measurement of an eye pressure had been completed, when the alignment has been accidentally completed with regards to that particular eye to be tested, an additional air pulse is discharged following the preceding air pulse discharge. Particularly, in the case of an eye to be tested which tends to largely fluctuate the sight fixation, or in the case of a baby or a child who has only a small capability of fixing his sight and tends to look aside, since a completion and a non-completion of an alignment are repeated within an extremely short time, air pulses are successively discharged each time, which likely renders pain and/or an unpleasant feeling to the patient. In addition, since an additional air pulse is discharged following the preceding air pulse discharge before the cylinder of the afore-mentioned apparatus has intaken a desired amount of air, an error or errors are occur in eye pressure measuring value.

SUMMARY OF THE INVENTION

An object of the present invention is to provide a noncontact type tonometer, in which the above-mentioned inconveniences of the conventional apparatus are eliminated.

Another object of the present invention is to provide a noncontact type tonometer, in which a fluid discharge based on an accidental alignment completion can be prevented.

A further object of the present invention is to provide a noncontact type tonometer, in which a fluid discharge based on an accidental alignment completion in the process where an additional fluid is discharged following the preceding fluid discharge, can be prevented.

A still further object of the present invention is to provide a noncontact type tonometer, in which an automatic discharge of a fluid based on an accidental alignment completion can be prevented under the condition that there is no presence of a command for discharging an additional fluid following the preceding fluid discharge.

A feature of the present invention can be found in a noncontact type tonometer having a controlling means for outputting an alignment completion signal, wherein the controlling means is adapted for monitoring an output of the alignment completion signal for a predetermined time and outputting a discharge command only when the alignment completion signal has continued for the predetermined time.

Another feature of the present invention can be found in a noncontact type tonometer having a controlling means for outputting an alignment completion signal, wherein the controlling means is provided with a delaying means so that a fluid discharge is not performed for a predetermined time from the preceding fluid discharge.

A further feature of the present invention can be found in a noncontact type tonometer having a controlling means for outputting an alignment completion signal, wherein there is provided a prohibiting means for prohibiting a fluid discharge based on the next following alignment completion signal under the condition that a fluid projecting switch adapted to discharge the next following fluid discharge is not operated after the preceding fluid discharge, so that a fluid discharge will not be automatically performed in succession.

Because of the above-described constitution of the present invention, there can be provided a noncontact type tonometer, wherein a fluid discharge due to an accidental alignment completion can be prevented before it occurs, no unpleasant feeling is rendered to the patient, and no measuring error results due to incomplete fluid discharge.

DETAILED DESCRIPTION OF THE EMBODIMENTS

Figure 1:
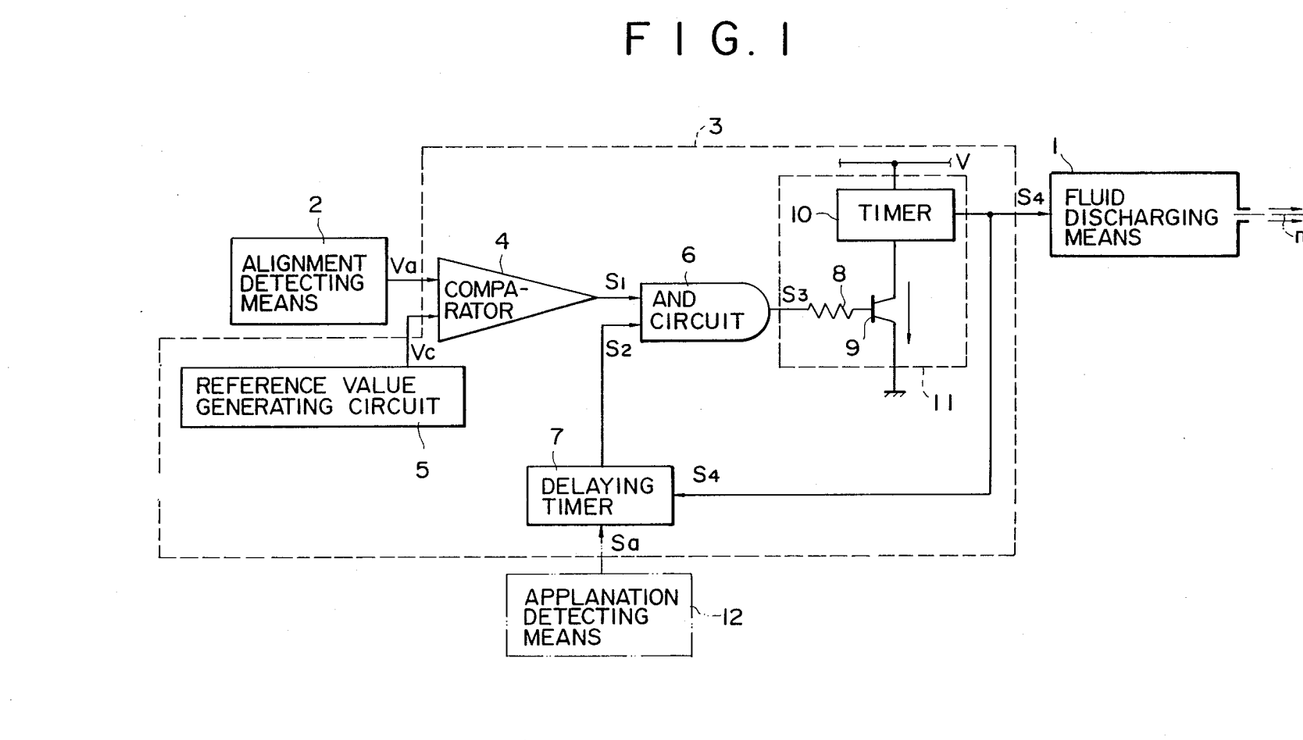
FIG. 1 is a block diagram showing a first embodiment of an important part of a noncontact type tonometer according to the present invention.

FIG. 1 illustrates a block diagram showing an important part of a noncontact type tonometer according to the present invention. In the figure, 1 denotes a fluid discharging means, 2 denotes an alignment detecting means, and 3 denotes a controlling means. The fluid discharging means 1 has such a function as to discharge an air pulse as a fluid towards the cornea of an eye to be tested (not shown). Since the constitution of the fluid discharging means 1 is the same as a conventional noncontact type tonometer, the description thereof will be omitted. Symbolic reference character m denotes the fluid discharging axis. The alignment detecting means 2 has such a function as to detect an alignment between the fluid discharging axis m and the vertex of the cornea, and to output a target detecting signal Va as an alignment signal. The alignment detecting means 2 has a photoelectrically inverting element (not shown). The target detecting signal Va is output by the photoelectrically inverting element. This photoelectrically inverting element corresponds to one which is disclosed in Japanese patent publication No. 58-34128, or one which is described in the United States patent application Ser. No. 801,960 which has been filed by Katsuhiko Kobayashi on Nov. 26, 1985 and has been assigned to the same assignee of the present application. The controlling means 3 has such a function as to determine whether or not the alignment has been completed upon receipt of the target detecting signal Va, and to output an alignment completion signal $S_1$ when the alignment has been completed.

The controlling means 3 includes a comparator 4 and a reference value generating circuit 5. The target detecting signal Va is input in one terminal of the comparator 4 and a reference voltage Vc is incurred to the other terminal thereof. This reference voltage Vc is used for determining whether or not there is alignment between the fluid discharging axis m and the vertex of the cornea. The comparator 4 compares the reference voltage Vc with the target detecting signal Va, and outputs an alignment completion signal $S_1$ of H level from the output terminal determining that the alignment has been completed when the amplitude of the target detecting signal Va is larger than the reference voltage Vc.

The output terminal of the comparator 4 is connected with one terminal of an AND circuit 6, and the other terminal of the AND circuit 6 is connected with the output terminal of a delaying timer 7. The delaying timer 7 has a normally closed contact (not shown). The normally closed contact is closed when the delaying timer 7 is not counting but opened when the delaying time 7 is counting. The delaying timer 7 is adapted to output a prohibiting signal $S_2$. The meaning of the prohibiting signal $S_2$ and the function of the delaying timer 7 will be described hereinafter. The prohibiting signal $S_2$ is output towards the AND circuit 6 through the normally closed contact. The prohibiting signal $S_2$ has a high H level when the delaying timer 7 is not counting and a low L level when the delaying timer 7 is counting. A count starting signal for causing the delaying timer 7 to start counting will be described hereinafter.

The output terminal of the AND circuit 6 is connected to a base of a transistor 9 through a resistor 8. In the AND circuit 6, the output terminal thereof becomes H level and outputs an actuating signal $S_3$ for actuating the transistor 9 when the alignment completion signal $S_1$ and the prohibiting signal $S_2$ of H level have been input. The transistor 9 functions as a switching circuit for controlling the counting of the timer 10. As for the timer 10, a power-on reset-type timer is used in this embodiment. Every time the transistor 9 is actuated and the power is turned on, the content so far counted is cleared so as to be ready for a new counting procedure.

The timer 10 outputs an action command signal $S_4$ for starting a fluid discharge towards the fluid discharging means 1 and also towards the delaying timer 7 after a predetermined time has been counted. The predetermined time is set to 0.2 seconds taking into consideration the minor fluctuation of the fixation of sight of the eye to be tested, etc. in this embodiment. When the action command signal $S_4$ has been input, the fluid discharging means 1 automatically performs a fluid discharge. As a result, an air pulse is projected towards the cornea of the eye to be tested.

Even if the alignment completion signal $S_1$ should be output from the comparator 4 because of inaccurate alignment or caused by accidental reasons such as patient's side-looking, minor fluctuation of the fixation of sight of the eye to be tested, or the like, the alignment completion signal $S_1$ would become instantaneously H level for 0.2 seconds or less. Accordingly, the output terminal of the comparator 4 would become L level a the next instant and the transistor 9 would stop working in the midway of the counting of the timer 10 for a predetermined time. Accordingly, the action command signal $S_4$ would not be output from the timer 10, and an eye pressure measurement based on accidental reasons such as minor fluctuation of the fixation of sight, etc., can be prevented.

That is, the transistor 9 and the timer 10 keep monitoring the alignment completion state for a predetermined time based on the alignment completion signal, and function as a monitoring means 11 for outputting the action command signal $S_4$ towards the fluid discharging means 1 only when the alignment completion state has been maintained for the predetermined time.

In the present embodiment, the action command signal $S_4$ also functions as a count starting signal for the delaying timer 7. The delaying timer 7 starts counting based on the action command signal. The delaying timer 7 functions as a delaying means (preventing means) for delaying the next following fluid discharge from the preceding fluid discharge for a predetermined time, so that the next following fluid discharge will be delayed for the predetermined time from the preceding fluid discharge after a successive fluid discharge. In the present embodiment, the afore-mentioned predetermined time of the delaying timer 7 is set to 2 to 5 seconds taking into consideration the time required for a desired amount of air to be intaken into an unshown cylinder of the apparatus of the fluid discharging means 1. The delaying timer 7 stops counting and opens the normally closed contact after the afore-mentioned predetermined time has elapsed. The prohibiting signal $S_2$ outputted from the timer 7 prohibits a the start of counting of the timer 10 for performing the next following fluid discharge after the successive fluid discharge for a predetermined time.

That is, when the normally closed contact is opened and the delaying timer 7 starts counting by the action command signal $S_4$, the prohibiting signal $S_2$ becomes L level for a predetermined time, the output terminal of the AND circuit 6 becomes L level, the transistor 9 is put off, and the timer 10 stops counting. Accordingly, during the counting of the delaying timer 7, even if the alignment completion is determined, and the alignment completion signal $S_{1a}$ output, and, as a result, the alignment completion state is maintained for more than the predetermined time, i.e., 0.2 seconds, the action command signal $S_4$ would not be output from the timer 10. Accordingly, the next following fluid discharge by the fluid discharging means 1 would be prohibited, and the next following fluid discharge would not be performed for the predetermined time during which a desired amount of air is intaken into the cylinder from the preceding fluid discharge. Thus, an incomplete successive discharge of fluid can be prevented.

Although the action command signal $S_4$ is used as means for causing the delaying timer 7 to start counting in the present embodiment, an applanation detecting signal Sa outputted from an applanation detecting means 12 known per se, may be used as means for causing the delaying timer 7 to start counting.

Likewise, although a fluid discharge of the fluid discharge means 1 is performed based on the action command signal $S_4$ of the monitoring means 11 in the present embodiment, the present invention is not necessarily provided with the monitoring means 11. In that case, the fluid discharge is started based on the actuating signal $s_3$ of the AND circuit 6. At that time, even if alignment completion signals are successively output because of accidental reasons such as minor fluctuation of the fixation of sight of the eye to be tested, the patient's side-looking, etc., and the alignment completion state is not maintained for a predetermined time, the fluid discharge would be performed. However, if the fluid discharge is performed, the next following fluid discharge would be prohibited for a predetermined time from the preceding fluid discharge.

Figure 2:
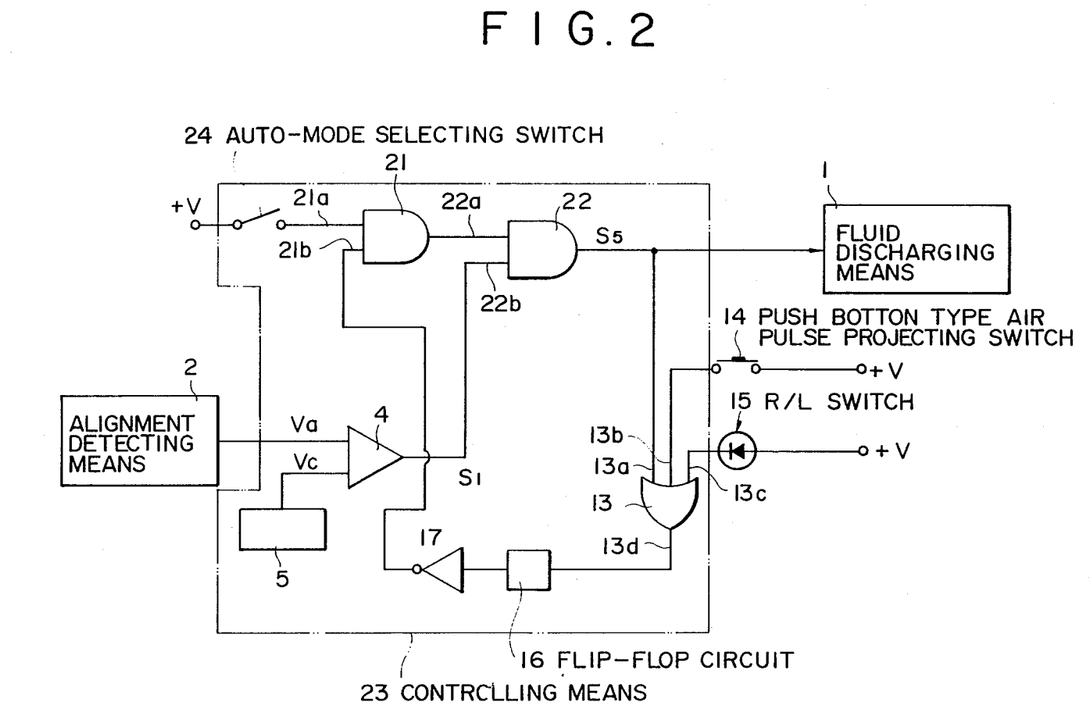
FIG. 2 is a block diagram showing a second embodiment of an important part of a noncontact type tonometer according to the present invention.

A second embodiment of the present invention will now be described with reference to FIG. 2, in which an important circuit part of a noncontact type tonometer according to the present invention is illustrated in the form of a block diagram. In the figure, 1 denotes a fluid discharging means known per se, 2 denotes an alignment detecting means known per se, 4 denotes a comparator, 5 denotes a reference value generating circuit, and 23 denotes a controlling means. Same component elements to the first embodiment are denoted by same reference numerals and a description thereof will be omitted.

A controlling means 23 is provided with an auto-mode selecting switch 24, a first AND circuit 21, a second AND circuit 22, an OR circuit 13, a flip-flop circuit 16, an inverter 17 and, a toggle switching means, etc.

The auto-mode selecting switch 24 is connected with an input terminal 21a of the first AND circuit 21. The input terminal 21b is connected with an output terminal of the inverter 17. An output terminal of the first AND circuit 21 is connected with one input terminal 22a of the second AND circuit 22. The other input terminal 22b of the second AND circuit 22 is connected with an output terminal of the comparator 4. The output terminals of the second AND circuit 22 are connected with the fluid discharging means 1 and an input terminal 13a of the OR circuit 13, respectively.

An input terminal 13b of the OR circuit 13 is connected with, for example, a push button type air pulse projecting switch 14 which can be manually operated. An input terminal 13c is connected with a R/L switch 15 comprising a photoelectric switch which will be described hereinafter. The R/L switch 15 functions as detecting means for detecting whether the eye to be tested is a right eye or a left eye.

An output terminal 13d of the OR circuit 13 is connected with the flip-flop circuit 16. An output terminal of the flip-flop circuit 16 is connected with an input terminal of the inverter 17.

Figure 3:
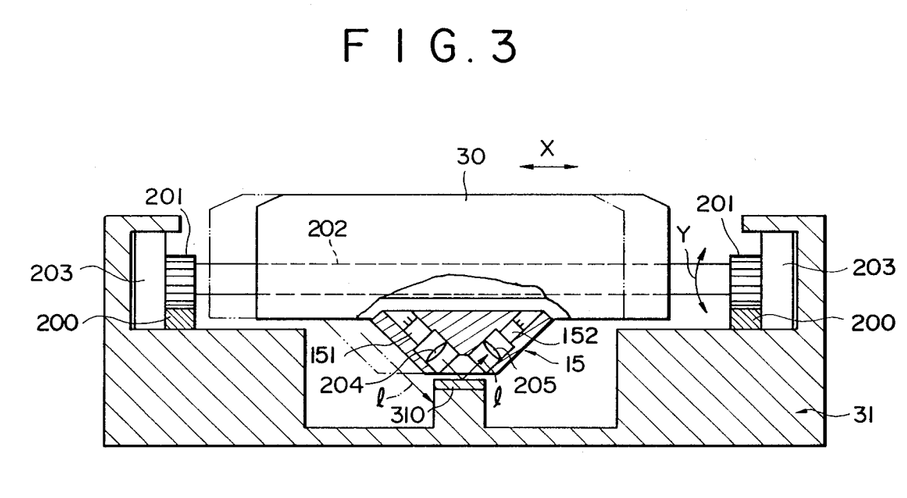
FIG. 3 is a sectional view showing a R/L switch of FIG. 2.

The R/L switch 15, as is shown in FIG. 3, includes a light emitting diode 151 and a light receiving diode 152. The R/L switch 15 is mounted on a bottom portion of a moving table 30 for supporting the main body of a tonometer (not shown). The moving table 30 is movable back and forth, and rightwards and leftwards on a framework 31 by a joy stick (not shown). In the figure, an arrow X shows the rightward and leftward movement of the moving table 30, while an arrow Y shows the turning direction for moving the moving table 30 in the back and forth direction. The framework 31 is provided with a reflecting mirror 310 for reflecting a light from the light emitting diode 151 towards the light receiving diode 152 when the moving table 30 is in the central position during its movement in the rightward and leftward direction. Reference numeral 200 denotes a rack, 201 denotes a gear, 202 denotes a guiding rod, and 203 denotes a roller which are assembled to construct driving means as known manner, and 204 and 205 denote lenses.

With the above-described configuration when the moving table 30 passes the central position on the framework 31 during its rightward and leftward movement, a light l from the light emitting diode 151 is reflected towards the light receiving diode 152, and the reflect light from the light emitting diode 151 is reflected towards the light receiving diode 152, and the reflecting light is detected.

Figure 4:
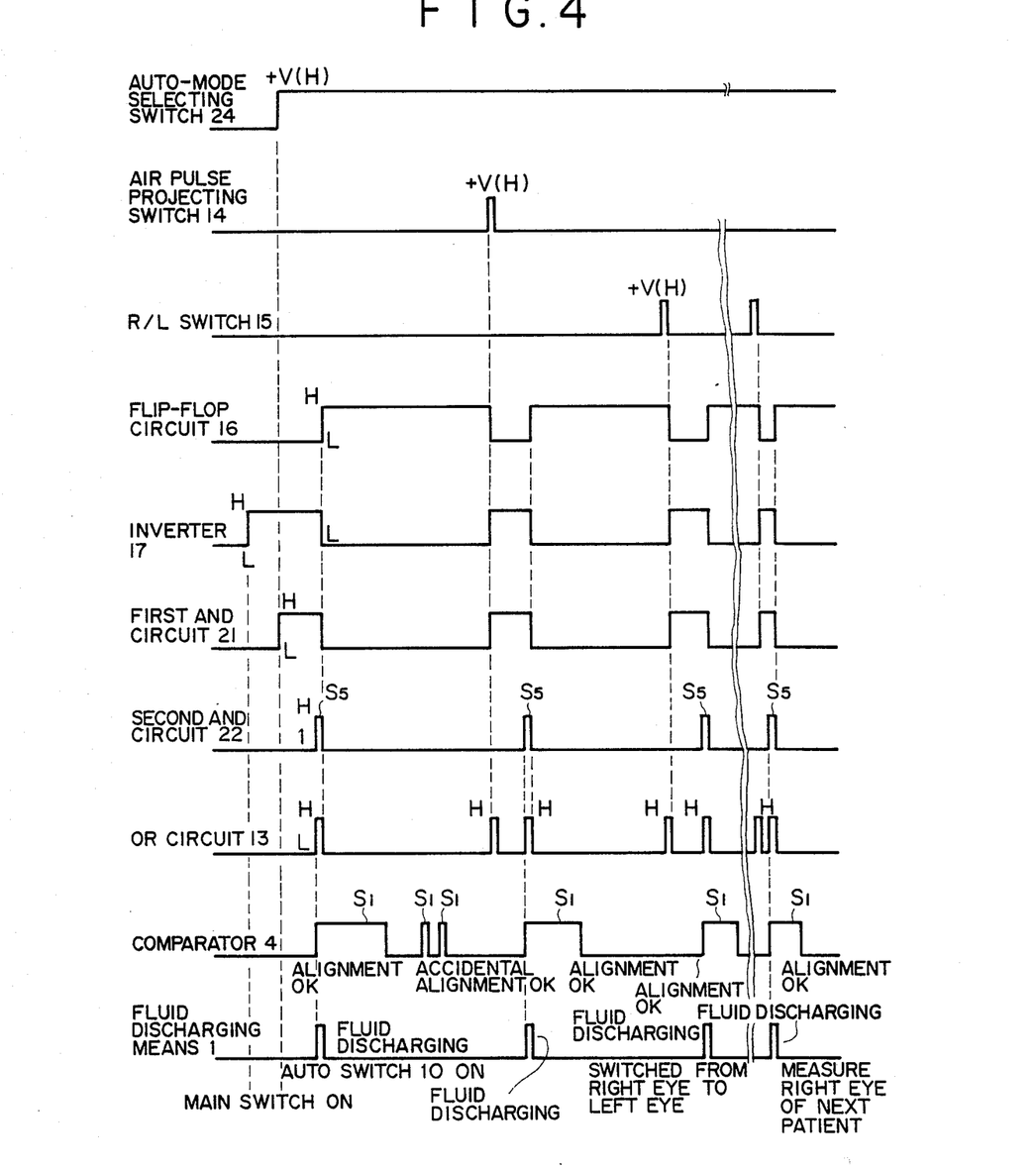
FIG. 4 is a timing chart showing one example of the operation of the noncontact type tonometer of FIG. 2.

The operation of a noncontact type tonometer according to the present embodiment will now be described with reference to the timing flow chart of FIG. 4.

A. Automatic Projecting Operation of Air Pulse

When a main switch (not shown) is put on, the output of the inverter 17 becomes H level and is input in the input terminal 21b of the first AND circuit 21. Then, when the operator puts the auto-mode selecting switch 24 on, the input terminal 21a of the first AND circuit 21 becomes H level. Since both the inputs of the first AND circuit 21 become H level by putting the auto-mode selecting switch 24 on, the output becomes H level. As a result, the input terminal 22a of the second AND circuit 22 becomes H level. When an alignment between the fluid discharging means 1 of the tonometer and the eye to be tested has been completed by moving the moving table 30, the comparator 4 is input with the alignment completion signal $S_1$ through the input terminal 22b of the second AND circuit 22. As a result, the output terminal of the second AND terminal 22 also becomes H level. Accordingly, the command signal $S_5$ (action command signal) of H level for causing the second AND circuit 22 to start a fluid discharge is output to the fluid discharging means 1, the fluid discharging means 1 is actuated, and an air pulse is projected towards the eye to be tested. Simultaneously, since the command signal $S_5$ from the second AND circuit 22 is input in the OR circuit 13, the output terminal of the OR circuit 13 becomes H level. As a result, the flip-flop circuit 16 becomes H level. The flip-flop circuit 16 maintains this H level state until the next input is performed.

The H-level output of the flip flop circuit 16 is inverted to L level by the inverter 17 and is input into the input terminal 21b of the first AND circuit 21. Accordingly, the output of the first AND circuit 21 becomes L level, and therefore the input terminal 22a of the second AND circuit 22 becomes L level. Since the foregoing state is maintained while the flip-flop circuit 16 is in H level, even if the alignment completion signal $S_1$ based on the establishment of an accidental alignment because of such reasons as, for example, minor fluctuation of the fixation of sight of the eye to be tested, etc., should be input into the second AND circuit 22, the fluid discharging means 1 would not be actuated because the command signal $S_5$ of the second AND circuit becomes L level.

B. Remeasuring Operation

When the user of the apparatus wants to remeasure the same eye which has been once tested, he may simply put the projecting switch 14 on. When this remeasuring command has been input, the output of the OR circuit 13 becomes H level, and is input into the flip-flop circuit 16. Since the flip-flop circuit 16 is switched from the H level state to the L level state by the input from the OR circuit 13, the input from the inverter 17 into the input terminal 21b of the first AND circuit 21 becomes H level. As a result, the input terminal 22a of the second AND circuit 22 also becomes H level, and the fluid discharging means 1 becomes ready to discharge a fluid. When the alignment completion signal $S_1$ is input, the command signal $S_5$ of the second AND circuit 22 becomes H level, and the fluid discharging means 1 is actuated. Simultaneously, the command signal $S_5$ from the second AND circuit 22 is output to the OR circuit 13. Due to the output of the OR circuit 13, the output level of the flip-flop circuit 16 is switched from L level to H level. Since the flip-flop circuit 16 maintains this state, the output of the inverter 17 becomes L level, the input terminal 21b of the first AND circuit 21 becomes L level, and the output of the first AND circuit 21 becomes L level. Accordingly, the command signal $S_5$ of the second AND circuit 22 also becomes L level irrespective of the alignment completion signal $S_1$. Accordingly, the fluid discharging means 1 is held in its non-operated state.

That is, the first AND circuit 21, the second AND circuit 22, the flip-flop circuit 16, and the inverter 17 function as a prohibiting means (preventing means) for prohibiting the fluid discharge based on the next following alignment completion signal $S_1$ under the condition that the fluid projecting switch 14 is not operated after the fluid discharge based on the preceding alignment completion signal $S_1$, even if the alignment signals $S_1$ should be output successively.

C. Switching of Eye to be Tested

When the moving table 30 is moved in the left direction in order to measure one of a patient's eyes, for example, a left eye after a right eye has been measured, the R/L switch 15 is put on. When the R/L switch 15 has been put on, the output of the OR circuit 13 becomes H level, and the output of the flip-flop circuit 16 becomes L level from H level. Accordingly, the inverter 17 becomes H level from L level, and the output of the first AND circuit 21 becomes H level. The following operation is performed in the same procedure to the afore-mentioned "A. Automatic Projecting Operation of Air Pulse".

When an eye pressure for a new patient is to be measured after an eye pressure for a patient has been measured, the moving table 30 is moved again and the main body of the apparatus is moved in order to measure the right eye. Due to the afore-mentioned movement, since the R/L switch 15 is put on again, the output of the OR circuit 13 becomes H level, the flip-flop circuit 16 becomes L level from H level, and the inverter 17 becomes H level from L level. Accordingly, the output of the first AND circuit 21 becomes H level. When the alignment completion signal $S_1$ is input into the second AND circuit 22 in the same procedure to the afore-mentioned automatic projecting operation of air pulse, an air pulse is automatically projected. That is, the first AND circuit 21, the second AND circuit 22, the flip-flop circuit 16, and the inverter 17 function as a prohibiting means for prohibiting the next following fluid discharge under the condition that the R/L switch 15 as a detecting means does not detect the movement of the main body (moving table 30) of the tonometer after a fluid discharge based on the preceding alignment completion signal $S_1$, even if the alignment completion signals $S_1$ should be output successively.

What is claimed is:

1. A noncontact type tonometer comprising:
   fluid discharging means for discharging a fluid towards the cornea of an eye to be tested along an axis thereof;
   alignment detecting means for detecting an alignment between the axis of said fluid discharging means and the vertex of said cornea, and for outputting an alignment signal when the alignment occurs;
   alignment completion determining means for determining whether or not the alignment had been completed upon receipt of the alignment signal from said alignment detecting means and outputting an alignment completion signal when the alignment has been completed; and controlling means for outputting an action command signal for automatically performing the fluid discharge of said fluid discharging means based on the alignment completion signal, said controlling means being provided with a delaying means for delaying an outputting time point of an action command signal for a next following fluid discharge with respect to an outputting time point of the action command signal for a preceding fluid discharge, so that the next following fluid discharge will be prohibited for a predetermined time from the preceding fluid discharge.

2. A noncontact type tonometer as claimed in claim 1 wherein said delaying means is a delaying timer for starting the counting based on the action command signal of the preceding fluid discharge.

3. A noncontact type tonometer as claimed in claim 1, wherein said delaying means includes an applanation detecting means for detecting an applanation of the cornea and a delaying timer for starting the counting based on an applanation detecting signal output from said applanation detecting means.

4. A noncontact type tonometer as claimed in claim 1, wherein said controlling means is further provided with a monitoring means for outputting an action command signal only when the alignment completion state has been maintained for a predetermined time.

5. A noncontact type tonometer as claimed in claim 4, wherein said monitoring means comprises a timer for starting the counting every time the alignment completion signal is input.

6. A noncontact type tonometer comprising;

fluid discharging means for discharging a fluid towards the cornea of an eye to be tested along an axis thereof;

alignment detecting means for detecting an alignment between the axis of said fluid discharging means and the vertex of said cornea, and for outputting an alignment signal when the alignment occurs; and controlling means for determining whether or not the alignment has been completed upon receipt of the alignment signal from said alignment detecting means, outputting an alignment completion signal when the alignment has been completed and outputting an action command signal based on said alignment completion signal, the fluid automatically discharge from said fluid discharging means in response to said action command signal; said controlling means including a manually operated fluid projection switch provided with a plurality means for prohibiting a fluid discharge based on the next following alignment completion signal such that said fluid projecting switch for discharging the next following fluid discharge is not operated after the fluid discharge based on the preceding alignment completion signal, even if the preceding and next following alignment completion signals have been output successively.

7. A noncontact type tonometer as claimed in claim 6, wherein said prohibiting means includes a R/L switch for switching a tonometer to a right side or a left side, the prohibition of a fluid discharge being canceled by said R/L switch.

* * * * *

UNITED STATES PATENT AND TRADEMARK OFFICE
CERTIFICATE OF CORRECTION

PATENT NO. : 4,872,460
DATED : October 10, 1989
INVENTOR(S) : Kouji Nishio; Yoshihiko Hanamura It is certified that error appears in the above-identified patent and that said Letters Patent is hereby corrected as shown below:

IN THE CLAIMS:

Claim 6, column 10, lines 17-18: "automatically discharge" should be --being automatically discharged--.

Claim 6, line 21: "projection" should be --projecting--; and "plurality" should be --prohibiting--.

Signed and Sealed this

Twenty-first Day of May, 1991

Attest:

HARRY F. MANBECK, JR.

*Attesting Officer*  *Commissioner of Patents and Trademarks*